United States Patent [19]

Karsten et al.

[11] 3,946,016
[45] Mar. 23, 1976

[54] FUNGICIDAL 8-QUINOLYL CARBANILATES

[75] Inventors: Kenneth S. Karsten, Westport; Joseph V. Karabinos, Orange, both of Conn.

[73] Assignee: R. T. Vanderbilt Company, Inc., East Norwalk, Conn.

[22] Filed: Mar. 16, 1973

[21] Appl. No.: 342,048

[52] U.S. Cl............ 260/287 L; 260/283 S; 252/107; 424/258
[51] Int. Cl.² ........................................ C07D 215/34
[58] Field of Search ................ 260/287 RL; 287 OX

[56] References Cited
UNITED STATES PATENTS

| | | | |
|---|---|---|---|
| 3,031,373 | 4/1962 | Schisla et al. | 260/287 R |
| 3,100,175 | 8/1963 | Bourquin | 260/287 R |
| 3,351,525 | 11/1967 | Hodel | 260/287 O X |
| 3,362,960 | 1/1968 | Hodel | 260/287 R |
| 3,488,376 | 1/1970 | Ulrich | 260/453 |
| 3,538,099 | 11/1970 | Rohr et al. | 260/287 R |

FOREIGN PATENTS OR APPLICATIONS

| | | | |
|---|---|---|---|
| 1,087,122 | 3/1966 | United Kingdom | 260/287 |
| 1,510,067 | 12/1966 | France | 260/287 O X |

Primary Examiner—Richard J. Gallagher
Assistant Examiner—David E. Wheeler
Attorney, Agent, or Firm—Roland T. Bryan

[57] ABSTRACT

Fungicidally and bactericidally active compounds of the formula

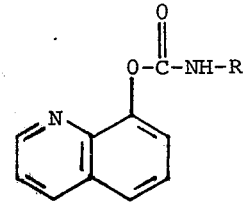

where R is allyl, cyclohexyl, naphthyl and preferably,

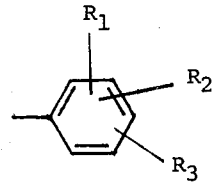

where $R_1$ is methoxy, ethoxy, methylthio, ethoxycarbonyl; $R_2$ is H, methoxy, chloro, methyl, nitro; $R_3$ is H, chloro. The compounds are used as fungistats and bacteriostats in soap and shampoo formulations and as preservatives in various industrial preparations. Certain di-8-quinolyl esters of arylenedicarbamic acid and poly(8-quinolyl esters) of carbanilic acid are found to possess activity against bacteria and fungi.

2 Claims, No Drawings 3,946,016

FUNGICIDAL 8-QUINOLYL CARBANILATES

BACKGROUND OF THE INVENTION

1. Field of the Invention

This invention relates to 8-quinolyl carbanilates and particularly selected novel 8-quinolyl esters of carbanilic acid and di-8-quinolyl esters of arylenedicarbamic acid possessing activity against a broad spectrum of bacteria and fungi, as well as methods for the preparation thereof.

The compounds of this invention find advantageous biostatic utility as fungistats and bacteriostats in soap and shampoo formulations and as preservatives and/or disinfectants in various industrial and agricultural preparations.

2. Description of the Prior Art

Preparations containing certain 8-quinolyl and 8-quinaldyl carbamates and carbanilates as active ingredients for combatting pests have been described in U.S. Pat. No. 3,538,099. The use of 0-(2-lower alkyl-8-quinolyl) N-methylcarbamate as an insecticide was suggested in U.S. Pat. No. 3,384,538. In addition the bactericidal and bacteriostatic properties of certain 8-hydroxyquinoline derivatives have been generally known.

Nevertheless, notwithstanding the known utility of certain compounds it remains impossible to predict the biological activity of a member of a chemical class such as 8-quinolyl or 8-quinaldyl carbamates and carbanilates from the performance of certain members of that class. Thus, U.S. Pat. No. 3,384,538 points out that the insecticidal and acaricidal properties of 0-(2-methyl-8-quinolyl) N-methylcarbamate are particularly surprising in view of the fact that the isomeric 2-methyl-5-quinolyl N-methylcarbamate fails to show such activities.

However, there exists an ever increasing need for compounds having fungicidal and bactericidal properties for use in various industrial, agricultural, medical and consumer applications. The need for developing a diversity of such compounds becomes particularly important when taking into consideration the necessity of evaluating as great a number as possible to ascertain those which will comply with requirements of safety, overall effectiveness, compatibility with environmental needs and the like while affording an alternative source of compounds for remedial preparations.

SUMMARY OF THE INVENTION

We have discovered that antimicrobic and antifungal properties against gram positive and gram negative organisms and fungi are exhibited by compounds of the general formulae (I)
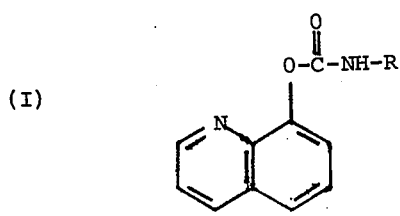

where R is allyl, cyclohexyl, naphthyl and preferably

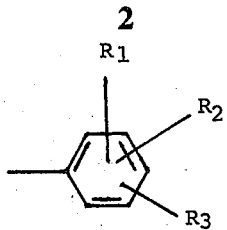

where $R_1$ is methoxy, ethoxy, methylthio, ethoxycarbonyl; $R_2$ is H, methoxy, chloro, methyl, nitro; $R_3$ is H, chloro; Or (II)
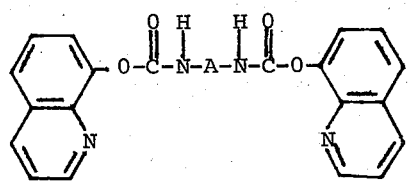

where A is phenylene and phenylene substituted by alkyl groups.

In addition, poly(8-quinolyl esters) of carbanilic acid such as poly(8-quinolyl ester) of polymethylene polycarbanilic acid display fungicidal and bactericidal activity.

The compounds of the general Formula I and II can be prepared according to known methods of reacting 8-hydroxyquinoline with a selected isocyanate in the presence or absence of an organic amine catalyst, to yield the appropriate carbamate or carbanilate. Particularly useful as reactive intermediates herein are isocyanates of the formula R-N=C=O where R has the same meaning as in Formula I including the novel chlorinated alkoxy aromatic isocyanates disclosed in copending patent application Ser. No. 317,006 filed Dec. 20, 1972, by J. V. Karabinos and John F. Cronan, for "Novel Isocyanates And Process For Preparing Same".

Thus it is an object of this invention to provide 8-quinolyl derivative compounds possessing fungicidal and bactericidal activity against a broad spectrum of bacteria and fungi.

Beneficially, it has been found that the compounds of this invention do not lose their bactericidal and fungicidal activity in the presence of detergents and, furthermore, possess effective skin substantivity, even after washing and rinsing. Hence, it is a further object of this invention to provide novel shampoo or soap cleansing agent compositions, and methods of use thereof, containing, as active agents, the compounds of this invention, that are substantive to the skin and are adapted to give prolonged effect in reducing the number of microorganisms on skin. These compositions can be formulated to include various detergents of the anionic, cationic, nonionic and amphoteric type.

Industrial products including adhesives, glue, organic binders, paints, paper, emulsions, polymers, dyeing and printing pastes, thickeners, organic products such as soya flour, wheat flour, and starch may be preserved and/or disinfected with the compounds of this invention. The compounds can also be used for protecting leather fibers and textiles as well as for slime control agents in various aqueous industrial systems and in paper manufacture. Another object of the invention, therefore, is the provision of preservatives and/or disinfectants, and methods of use thereof, for industrial and agricultural products subject to attack by gram positive and gram negative bacteria and fungi.

The compounds according to Formulae I and II may be advantageously used in formulations and preparations in areas where bactericidal and fungicidal activity is desired. Thus the compounds of the invention may be incorporated, in accordance with the methods known in the art, into a wide variety of forms exemplary of which are solid forms such as dusts, sprinkling agents and coated granules, dispersible concentrates including emulsions, pastes and wettable powders as well as solutions, aerosols and the like. Thus, the compounds may be readily included, as active agents, in consumer products including cleansing agents such as toilet soaps, shampoos, synthetic laundry detergents and aerosols. The amount of the active agent required will vary with the microbicidal, fungicidal or biostatic effect sought, the utility of the treated material and the type and dimensions of the material treated. Therefore, no rigid limits of the quantity required can be here set forth, it being understood that those skilled in the art will be able to determine, according to known practice, what the effective amount for any given application must be.

DESCRIPTION OF THE PREFERRED EMBODIMENTS

The following examples are illustrative of embodiments of the invention.

EXAMPLE 1

8-Hydroxyquinoline (14.5g) was dissolved in 150g acetonitrile under moderate warming. After addition of 3 drops triethylamine, as a catalyst, 11.9g phenyl isocyanate was added dropwise under stirring on an ice bath. The formed 8-quinolyl N-phenylcarbamate was recovered by filtration and washed with cold acetonitrile. The yield was 88.5% and the melting point 164.°C.

EXAMPLE 2

To 14.5g of 8-hydroxyquinoline dissolved in 70ml acetone was added 18.35g 4-chloro-2-methoxyphenyl isocyanate. The mixture was warmed until all solid isocyanate had dissolved. The reaction mixture was allowed to stand overnight. The quinolyl 4-chloro-2-methoxycarbanilate was collected by suction filtration, washed with 50:50 acetone-hexane solution and recrystallized from methanol. The melting point of the product was 146°–7°C. A 75% yield was obtained.

The following compounds may be prepared in a similar manner:

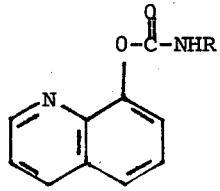

m.p. 107–9°C.

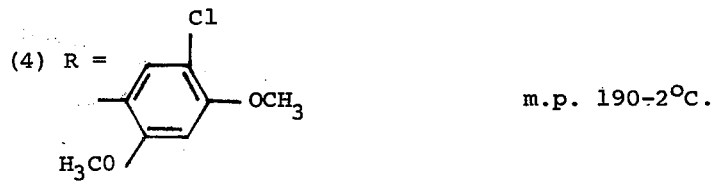

m.p. 190–2°C.

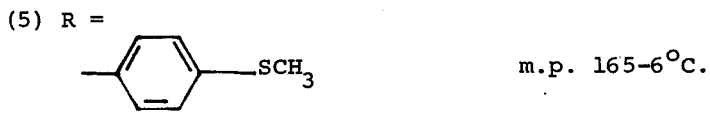

m.p. 165–6°C.

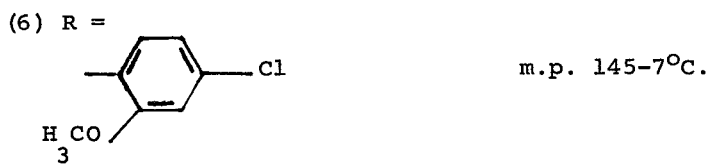

m.p. 145–7°C.

m.p. 148–9°C.

(8) R = 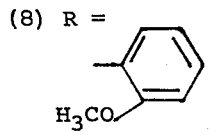 m.p. 117-8°C.
(9) R = 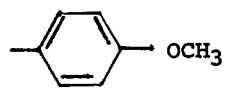 m.p. 136-8°C.
(10) R = 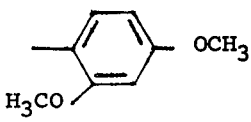 m.p. 146-8°C.
(11) R = 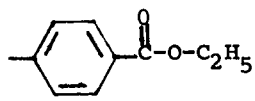 m.p. 210-12°C.
(12) R = 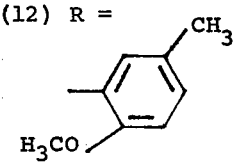 m.p. 126-8°C.
(13) R = 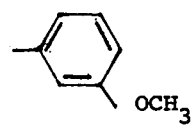 m.p. 135-7°C.
(14) R = 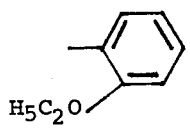 m.p. 107-9°C.
(15) R = 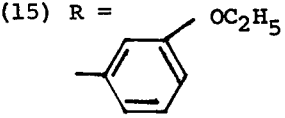 m.p. 173-5°C.
(16) R = 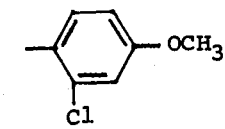 m.p. 110-3°C.
(17) R = 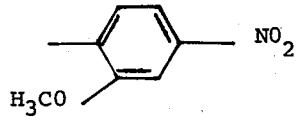 m.p. 178-9°C.

(18) R = 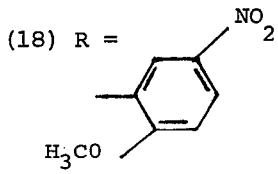   m.p. 197-9°C.

(19) R = -CH$_2$-CH=CH$_2$   m.p. 107-9°C.

(20) R = naphthyl   m.p. 124-6°C.

(21) R = cyclohexyl   m.p. 135-7°C.

and compounds of the formula

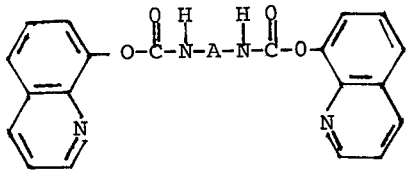

(22) A =    m.p. 125-7°C.

EXAMPLE 3

Microbicidal Activity a. Agar Incorporation Technique

The fungistatic efficacy of the compounds of this invention when in contact with growing fungi in artificial media was determined as follows. Stock solutions were prepared by dissolving test compounds either in water or in acetone and added to agar medium at 45°C. After hardening, agar was inoculated with spores of the fungus *Aspergillus niger*. The inoculated plates were incubated for 4 days at 28°C. and 95% relative humidity. The results, reported as the lowest parts per million of the test compound showing no growth or sporulation, are listed in Table 1 below.

b. Penicillin Button Assay

The antibacterial effect of the compounds of this invention was determined as follows. Penicillin buttons (13mm) were placed in test chemical solutions of various dilutions for 5 min., then removed and dried on paper towel. The buttons were placed on agar inoculated with *Bacillus subtilis*, *Staphylococcus aureus*, and *Salmonella typhosa* and incubated for 24 hrs. at 37°C. The results reported as lowest parts per million exhibiting the zone of inhibition, are listed in Table 1 below.

TABLE 1

| Active Substance | Lowest Effective Concentration (ppm) | | | |
|---|---|---|---|---|
| | A. niger | B. subtilis | S. aureus | S. typhosa |
| 8-Quinolyl carbanilate (control) | 100 | 100 | 100 | 100 |
| 8-Quinolyl 4-chloro-2-methoxycarbanilate | 100 | 50 | 100 | 100 |
| 8-Quinolyl 3-methylthiocarbanilate | 50 | 100 | 100 | 100 |
| 8-Quinolyl 5-chloro-2,4-dimethoxycarbanilate | 100 | 100 | 100 | 100 |
| 8-Quinolyl p-methylthiocarbanilate | 50 | 50 | 50 | 50 |
| 8-Quinolyl 5-chloro-2-methoxycarbanilate | 50 | 50 | 50 | 50 |
| 8-Quinolyl 2-methoxycarbanilate | 50 | 20 | 20 | 20 |
| 8-Quinolyl p-methoxycarbanilate | 50 | 20 | 50 | 50 |
| 8-Quinolyl 2,4-dimethoxycarbanilate | 50 | 20 | 50 | 20 |
| 8-Quinolyl 2-methoxy-5-methylcarbanilate | 50 | 20 | 50 | 50 |
| 8-Quinolyl m-methoxycarbanilate | 50 | 50 | 100 | 50 |
| 8-Quinolyl o-ethoxycarbanilate | 50 | 50 | 100 | 100 |
| 8-Quinolyl m-ethoxycarbanilate | 50 | 20 | 50 | 100 |
| 8-Quinolyl 2-methoxy-4-nitrocarbanilate | 100 | 50 | 100 | 100 |
| 8-Quinolyl 2-methoxy-5-nitrocarbanilate | 100 | 50 | 50 | 100 |
| 8-Quinolyl N-allylcarbamate | 100 | 50 | 100 | 50 |
| 8-Quinolyl N-naphthylcarbamate | 50 | 20 | 50 | 50 |
| 8-Quinolyl N-cyclohexylcarbamate | 100 | 100 | 300 | 100 |
| Di-8-quinolyl toluene-2,4-dicarbamate | 50 | 5 | 5 | 5 |
| Poly(8-quinolyl) polymethylene polycarbanilic acid ester | 100 | 300 | 300 | 300 |
| 8-Quinolyl 2-chloro-4-methoxycarbanilate | 100 | 100 | 300 | 100 |

The results set forth in Table 1 demonstrate the good microbicidal effect against bacteria and fungi possessed by the compounds of this invention. Considering the unsubstituted 8-quinolyl carbanilate as a control exhibiting good microbicidal activity, since displaying the desired effect at concentrations as low as 100ppm, the compounds of this invention show similar or, in most instances, even greater effectiveness. The unexpected effectiveness of the compounds of this invention is even more apparent when the results set forth in Table 1 are compared with the results set forth in Table 2 for structurally similar compounds. In particular the activity of the 8-quinolyl 4-chloro-2-methoxycarbanilate is surprising considering the lack of effectiveness of either the corresponding 8-quinaldyl derivative, 8-quinaldyl 4-chloro-2-methoxycarbanilate or the isomeric 5-isoquinolyl 4-chloro-2-methoxycarbanilate.

were similar to those obtained with a soap base. For example, the average diameter of the zone inhibited by 8-quinolyl 4-chloro-2-methoxycarbanilate as the active ingredient in shampoo was 8, 9 and 14 mm for *Bacillus subtilis*, *Staphylococcus aureus*, and *Salmonella typhosa*.

TABLE 2

(NEGATIVE RESULTS)

| Test Substance | Lowest Effective Concentration (ppm) | | | |
|---|---|---|---|---|
|  | A. niger | B. subtilis | S. aureus | S. typhosa |
| 8-Quinolyl N-dodecylcarbamate | +1M[1,2] | +10M | +10M | +10M |
| 8-Quinolyl N-octadecylcarbamate | +1M | 500 | 1M | 1M |
| Di-8-quinolyl hexamethylenedicarbamate | +1M | 10M | 10M | 10M |
| Di-8-quinolyl 4,4'-methylenebiscarbanilate | 500 | 10M | 10M | 10M |
| [3]8-Quinaldyl 4-chloro-2-methoxycarbanilate | 500 | 300 | +10M | +10 M |
| 2-(8-Quinolyloxy)ethyl 4-methyl-3-nitrocarbanilate | +1M | +10M | +10M | +10M |
| [3]5-Isoquinoly 4-chloro-2-methoxycarbanilate | 1M | +10M | +10M | +10M |

[1]+=No inhibition at highest level tested
[2]M=1000
[3]Compare compound No. 2, table 1

EXAMPLE 4

Bacteriostatic Activity and Hide Substantivity in Soap

An experimental study was conducted on the bacteriostatic activity of compounds of this invention in a soap base and also their resulting skin substantivity. In the soap plug test for bacteriostatic activity, 1% test material based on the weight of soap, was milled into "Ivory" soap (made according to U.S. Pat. No. 2,295,594) and compressed into plugs. Plugs (0.5 inch in diameter and 0.25 inch thick) of each of the test soaps were placed on agar plates seeded with one of three representative test bacteria, *Bacillus subtilis*, *Staphylococcus aureus*, and *Salmonella typhosa*. After incubation at 37°C. for 24 hrs., the clear zone of inhibition (lack of bacterial growth) was measured and reported as average diameter of zone inhibition (diameter of clear zone less the diameter of the soap plug). The results are tabulated in Table 3 below.

For the test of substantivity or retention of bacteriostat by the skin after washing with the test soap, untanned calf skin hide buttons were soaked in an 8% solution of the test soap containing 1% bacteriostat, rinsed four times with distilled water, placed on seeded agar plates and incubated for 24 hrs. at optimum temperature of the test bacteria, *Bacillus subtilis*, *Staphylococcus aureus* and *Salmonella typhosa*. The zones of inhibition were measured and reported as in the soap plug test. The results are tabulated in Table 3 below, also.

EXAMPLE 5

Preservation of Adhesives

The toxicant compounds of this invention were added in varying percentages to an adhesive formulation containing casein and soya flour. 8-quinolyl 3-methylthiocarbanilate and 8-quinolyl 2,4-dimethoxy-5-chlorocarbanilate in concentrations of 500 ppm showed excellent retarding properties with regard to formation of odor or spoilage, and consequently, inhibition of microorganism growth, for extended periods of time.

EXAMPLE 6

Inhibition of Slime Formation

As a slimicide test, penicillin assay filter paper discs were soaked in test solutions containing 50 ppm of compounds of this invention and placed on agar seeded with slime culture obtained from a cooling water system. The diameter of the zone inhibited by 50 ppm test sample is reported in Table 4, indicating excellent retardant properties.

TABLE 4

| Active Ingredient | Average Diameter of Inhibited zone in mm |
|---|---|
| 8-Quinolyl carbanilate (control) | 2 |
| 8-Quinolyl 3-methylthiocarbanilate | 4 |
| 8-Quinolyl 2,4-dimethoxy-5-chlorocarbanilate | 2 |

TABLE 3

| Active Ingredients | Average diameter of inhibited zone in mm | | | | | |
|---|---|---|---|---|---|---|
|  | Activity in Soap | | | Hide Substantivity | | |
|  | B. subtilis | S. aureus | S. typhosa | B. subtilis | S. aureus | S. typhosa |
| 8-Quinolyl 4-chloro-2-methoxycarbanilate | 22 | 13 | 10 | 11 | 10 | 7 |
| 8-Quinolyl 2-methoxycarbanilate | 23 | 21 | 16 | 12 | 10 | 10 |
| 8-Quinolyl 2-methoxy-5-methylcarbanilate | 20 | 15 | 16 | 8 | 14 | 5 |
| 8-Quinolyl 2-methoxy-4-nitrocarbanilate | 16 | 16 | 14 | 10 | 10 | 8 |
| 8-Quinolyl N-allylcarbamate | 28 | 20 | 24 | 12 | 16 | 10 |
| 8-Quinolyl N-naphthylcarbamate | 22 | 18 | 22 | 10 | 10 | 10 |
| 8-Quinolyl N-cyclohexylcarbamate | 22 | 18 | 16 | 10 | 12 | 8 |
| Di-8-quinolyl toluene-2,4-dicarbamate | 24 | 12 | 8 | 10 | 6 | 8 |

The tabulated results indicate successful bacteriostatic activity in soap and retention of bacteriostat on the skin after washing with such soap. The skin substantivity test was repeated by using a shampoo base according to the procedure set forth above. The results Thus, there has been disclosed a group of substituted 8-quinolyl and poly(8-quinolyl esters) of carbanilic acid and di-8-quinolyl esters of arylenedicarbamic acid, and methods of preparation thereof, possessing biocidal and biostatic activity against a broad spectrum of bacteria and fungi encountered in industrial, agricultural, medicinal and consumer areas.

We claim:

1. A compound of a formula

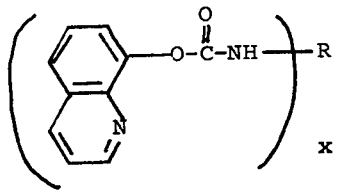

where $x = 1$, R is

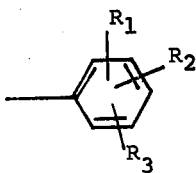

where $R_1$ is selected from the group consisting of methoxy, ethoxy and methylthio; $R_2$ is selected from the group consisting of H, methoxy, chloro, methyl or nitro; and $R_3$ is selected from the group consisting of H or chloro.

2. The compound, 8-Quinolyl-4-chloro-2-methoxycarbanilate.

* * * * *